United States Patent [19]

Armstrong

[11] 4,331,147
[45] May 25, 1982

[54] SYSTEM FOR DRAINING WOUNDS

[75] Inventor: Lee C. Armstrong, Atlanta, Ga.

[73] Assignee: Glasrock Products, Inc., Fairburn, Ga.

[21] Appl. No.: 164,923

[22] Filed: Jul. 1, 1980

[51] Int. Cl.³ .............................................. A61M 1/00
[52] U.S. Cl. ................................... 128/276; 128/275; 128/760
[58] Field of Search ............... 128/275, 276, 277, 278, 128/297, 349 R, 350 R, 760, 763, 764, 769, 770, 272; 215/DIG. 3, 364, 247, 249; 206/524.8

[56] References Cited

U.S. PATENT DOCUMENTS

| 3,074,541 | 1/1963 | Roehr | 128/276 UX |
| 3,486,539 | 12/1969 | Jacuzzi | 128/272 |
| 3,529,633 | 9/1970 | Vaillancourt | 128/349 R |
| 3,604,410 | 9/1971 | Whitacre | 128/276 |
| 4,246,899 | 1/1981 | Loseff | 128/276 |

OTHER PUBLICATIONS

"Continuous Suction in Hand Surgery", Lunseth, M.D. et al., Journal of Hand Surgery, 1979, pp. 193-194.
"An Inexpensive Wound Suction Device", Miller, M.D. et al., Surg. Cynical Obstet., vol. 141, p. 768, 1975.

Primary Examiner—Robert W. Michell
Assistant Examiner—J. L. Kruter
Attorney, Agent, or Firm—Lane, Aitken, Kice & Kananen

[57] ABSTRACT

A system for draining a wound including an elongated flexible catheter tube, an evacuated collection container and an adapter connecting the catheter tube to the container. The container has a pierceable stopper, and the adapter includes a projecting hollow needle and a pair of arcuate guide flanges disposed along opposite sides of the needle. As the adapter is moved into position on the container, the arcuate flanges move along the periphery of the stopper and the needle pierces the stopper. A graduated translucent protective tubular housing receives the container, the housing having arcuate internal surfaces frictionally engaging external surfaces of the guide flanges to retain the adapter in the housing. The adapter includes gripping portions extending beyond the housing and gaps exposing the stopper, so that the adapter may be removed from the container while the stopper is held in place. The drainage system is attached to the body of a patient by the housing, so that the container can be removed and replaced without disturbing the attachment.

14 Claims, 3 Drawing Figures

SYSTEM FOR DRAINING WOUNDS

BACKGROUND OF THE INVENTION

This invention relates to a system for draining surgical wounds, and more particularly, to a system including an evacuated collection container, a catheter tube, a protective housing for the catheter tube and an adapter for connecting the catheter tube to the evacuated container.

The prevention of hematoma is a major prerequisite of uncomplicated wound healing after the repair of a traumatic or surgically created wound. Despite meticulous technique in the care of such a wound, complete arrest of bleeding may not be achieved. Usually, gauze or rubber drains are used with a supportive dressing, but in recent years continuous suction drainage has been found to further reduce the risk of hematoma.

Known suction drainage systems for surgical wounds customarily include a catherter tube for insertion into the wound, a collection container for holding the fluid drained from the wound, and a connector for connecting the catheter tube to the container and providing fluid communication therebetween. In addition, a vacuum source is necessary to draw fluid from the wound into the collection container. The connector is typically a standard butterfly needle secured to extension tubing, which forms the catheter. The butterfly needle is inserted through a pierceable stopper on an evacuated container to make the connection, and the evacuated container is attached directly to the body of the patient.

However, problems arise with respect to the retention of the connector on the collection container. For example, in the butterfly needle system, as a result of movement of the patient, there is considerable wobbling of the needle with respect to the collection container stopper and the danger that, after extended wobbling, the needle will separate from the stopper. Furthermore, when the evacuated container is full, the attachment of the container to the body must be disturbed, so that the full container can be removed and a new container can be attached. In addition, the container is vulnerable to shattering or cracking due to impacts imposed by the movement of the patient.

SUMMARY OF THE INVENTION

It is therefore an object of the present invention to provide a system for draining a wound which is sterile, compact and light, and lends itself to attachment to the body of a patient.

It is a further object of the present invention to provide a system for draining a wound including a catheter tube and a collection container which has a self-contained source of vacuum and can be attached to the body of a patient at any location relative to the wound.

It is a still further object of the present invention to provide a system for draining a wound having an adapter for holding the catheter tube fixed with respect to the collection container, yet allowing easy connection and removal of the catheter tube with respect to the container.

It is an additional object of the present invention to provide a system for draining a wound including a housing for receiving and protecting the collection container and for engaging the adapter.

It is another object of the present invention to provide a system for draining a wound which permits monitoring of the amount and character of the fluid drained and easy replacement of the filled collection containers.

Toward the fulfillment of these and other objects, the drainage system of the present invention comprises an elongated flexible catheter tube having perforations at one end, and evacuated collection container having a pierceable stopper, and an adapter having a body including a base and a hub formed on the base, and a post defined on the hub for receiving the other end of the catheter tube. The adapter further includes a hollow needle embedded in and extending through the body and a pair of arcuate guide flanges disposed on opposite sides of the needle and extending from the base for engagement with the evacuated collection container and stopper. A translucent or transparent tubular protective housing is provided for receiving the container and frictionally engaging outer surfaces of the arcuate guide flanges. Graduations or other markings for measuring the volume of material received in the evacuated collection container can be included on the tubular housing. The catheter tube, container, adapter and housing may all be made of appropriate plastic materials. Furthermore, the entire system can be sterilized and enclosed in a sealed sterile package for shipment and storage.

Consequently, the drainage system is lightweight and the evacuated collection container may be attached in any location relative to the wound, since the vacuum in the container will permit drainage of the wound regardless of the location of the container. Furthermore, the engagement of the arcuate flanges of the adapter with the evacuated collection container and the stopper and the frictional retention of the arcuate flanges within the tubular housing prevent movement between the catheter tube and the container, while permitting ease of connection and removal of the catheter tube with respect to the container. Moreover, the tubular housing protects the container and permits visual inspection and measurement of the fluid collected in the container.

DETAILED DESCRIPTION OF THE PREFERRED EMBODIMENT

Figure 1:
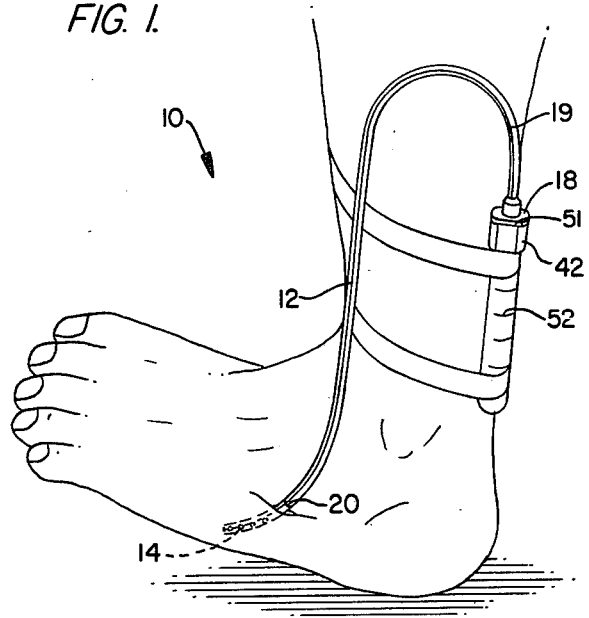
FIG. 1 is a perspective view of the drainage system of the present invention attached to a patient for draining a surgical wound in the foot.

As shown in FIG. 1, the wound drainage system according to the present invention, generally designated by the reference numeral 10, is attached to the leg of a patient just above the ankle for draining a surgical wound in the foot. The drainage system 10 includes an elongated flexible catheter tube 12 having a number of perforations 14 at an end of the tube which is inserted into the wound, an evacuated collection container 16 (FIG. 2), and an adapter 18 for connecting the unperforated end of the catheter tube 12 to the evacuated collection container 16. The evacuated collection container 16 can be positioned above the wound and still collect drainage from the wound, because the vacuum present in the container 16 will draw fluid upwardly from the wound and into the container 16. Although the drainage system 10 is shown collecting drainage from a wound in the foot, it will be apparent that the drainage system can be used for draining wounds in many other parts of the body, such as the leg, knee, hand, arm, breast, neck or face.

The catheter tube 12 is made of silicone rubber to resist the clotting of draining material in the bore of the tube 12. A radio-opaque stripe 19 runs the entire length of the catheter tube 12, so that the tube 12 may be easily located on a radiograph. An indicator mark 20 is located a suitable predetermined distance, such as 5 centimeters, from the perforations 14 to prevent the cathether tube 12 from being over-extracted from the wound, thereby exposing one or more perforations 14 to the air and causing the loss of suction.

Figure 2:
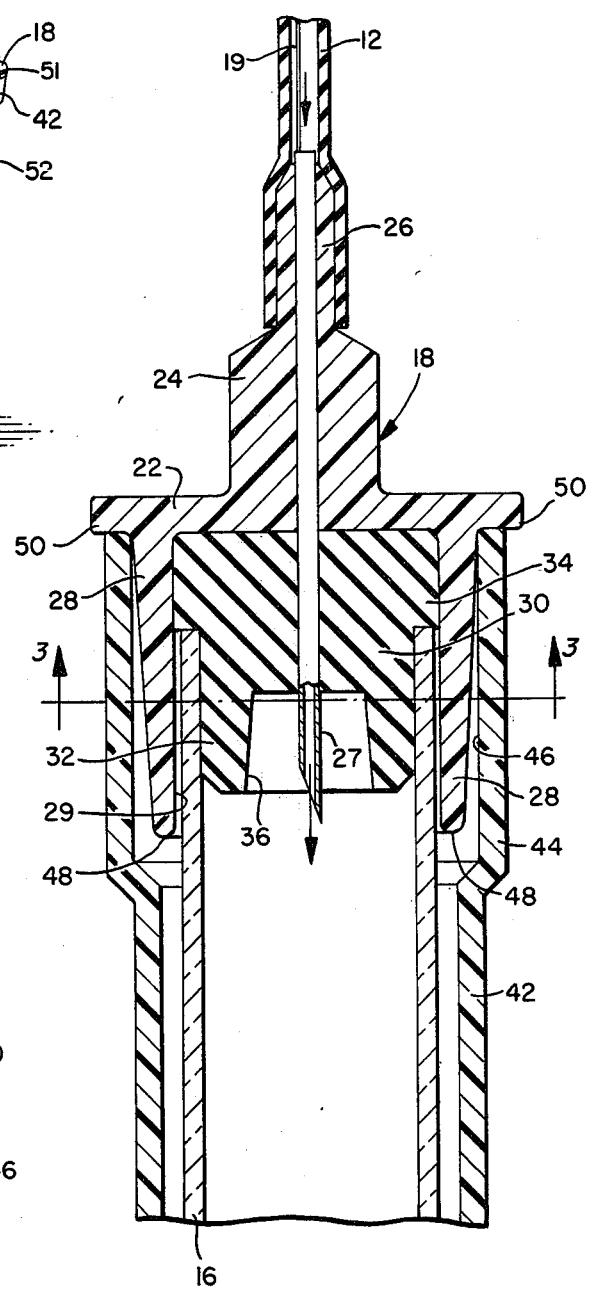
FIG. 2 is an enlarged cross-sectional view of a portion of the drainage system of FIG. 1.

The adapter 18, which is best illustrated in FIG. 2, includes a body having a base 22 and a hub 24 defined on the base 22. An attachment post 26 for receiving the unperforated end of the catheter tube 12 projects beyond the hub 24 and includes a conical portion at its outer end to guide the catheter tube 12, which stretches radially as it is forced onto the conical portion and is frictionally retained on the post 26. A hollow needle 27, which is embedded in and extends through the body of the adapter 18, has a point that projects well beyond the base 22 and a tail that extends slightly beyond the conical portion of the post 26. A pair of arcuate guide flanges 28 extend at substantially right angles from the base 22 and define a cradle for receiving the evacuated collection container 16. Internal surfaces 29 of the guide flanges 28 face one another from opposite sides of the needle 27, which defines the axis of curvature of the arcuate guide flanges 28. The guide flanges 28 serve to protect the needle 27 during non-use of the adapter 18 and during the connection of the adapter 18 to the evacuated container 16.

The guide flanges 28 are suited to secure the adapter 18 to the evacuated collection container 16, which is in the form of a tube having a closed end and an open end defining a rim. A stopper 30 of rubber or suitable elastomeric material is positioned in the open end of the tube. The stopper 30 includes a stem 32 fitting tightly within the open end of the tube and an integral flange 34 extending radially outwardly from the stem 32 and protruding slightly beyond the rim of the tube. The stem 32 may also include a depression, such as depression 36 in its bottom, to define a septum adapted for penetration by the needle 27 of the adapter 18. As the needle 27 is moved through the septum, the guide flanges 28 of the adapter 18 engage and slide along the outer surfaces of the flange 34 of the stopper 30 and the evacuated collection container 16, thereby maintaining the needle 27 parallel to the axis of the evacuated container 16 and reducing the wobble of the needle 27 in the septum.

The evacuated collection container 16 is preferably a standard cylindrical evacuated blood collection tube, which is sterile both inside and out. Such a tube allows for the fluid to be collected and transported for analysis without transfer into another container. In addition, the drainage system 10 can accommodate more than one size evacuated container. Thus, for example, an original 15 cc tube, when full, can be replaced by an empty 10 cc tube.

A tubular protective housing 42 is provided to enclose the evacuated collection container 16 and receive the adapter 18. The housing 42 has a closed end and an opening at the other end at which the diameter of the housing 42 is increased to define an enlarged peripheral wall 44 having an internal surface including a pair of opposed arcuate surfaces 46 and a pair of flat surfaces 47. The radius of curvature of the arcuate surfaces 46 is greater than the outer radius of the evacuated collection container 16. The guide flanges 28 of the adapter 18 are accommodated in spaces formed between the exterior surfaces of the evacuated container 16 and the arcuate surfaces 46 of the enlarged peripheral wall 44, wherein they firmly frictionally engage the arcuate surfaces 46.

Each arcuate guide flange 28 includes a free end 48 distal to the base 22 and a pair of lateral edges 49 extending between the free end 48 and the base 22. Between adjacent lateral edges 49 of the opposed guide flanges 28 are gaps which provide access to the flange 34 of the stopper 30 when the adapter 18 is in position on the evacuated collection container 16. The exterior surfaces of the guide flanges 28 are inclined toward the needle 27 at the free ends 48 of the flanges 28, the radius of curvature of the guide flanges 28 at their free ends 48 being slightly smaller than the radius of curvature of the arcuate surfaces 46 of the peripheral wall 44 of the housing 42 so that the guide flanges taper at their free ends 48. In addition, the radius of curvature of the outer surfaces of the guide flanges 28 at their juncture with the base 22 is slightly larger than the radius of curvature of the arcuate surfaces 46. Therefore, as the guide flanges 28 are inserted into the housing 42, they engage the arcuate surfaces 46 and are frictionally retained increasingly snugly against the arcuate surface 46.

Figure 3:
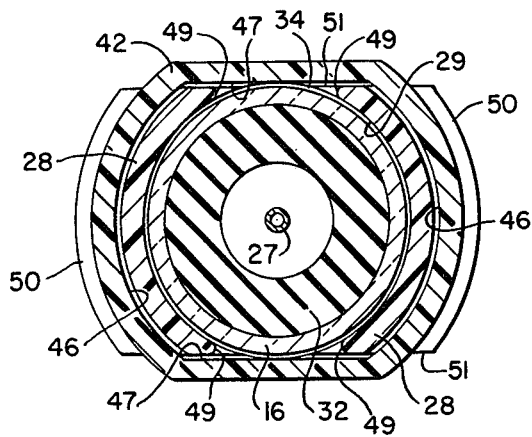
FIG. 3 is a cross-sectional view taken along the line 3—3 in FIG. 2.

The base 22 of the adapter 18 includes portions which extend laterally beyond the outer surfaces of the guide flanges 28 and beyond the peripheral wall 44 of the housing 42, thereby defining gripping formations 50 which enable the user to easily grip the adapter 18 for removal from the housing 42. Furthermore, the base 22 includes side surfaces 51, shown in FIGS. 1 and 3, which lie in planes defined by the adjacent edges 49 of the opposed guide flanges 28, so that the flange 34 of the stopper 30 is exposed to engagement by the fingers of a user, whereby the stopper 30 can be held in place on the evacuated collection container 16 when the adapter 18 is removed from the container 16. Thus, the user can reach the flange 34 to hold the stopper 30 in place on the evacuated collection container 16 with the fingers of one hand, while engaging the gripping formations 50 to remove the adapter 18 with the fingers of the other hand.

The tubular protective housing 42 may be formed from plastic or other suitable material and is preferably translucent or transparent, so that the amount and character of the contents of the evacuated container 16 may be visible therethrough. In addition, the housing 42 may include indicia 52 to enable the measurement of the volume of material gathered in the evacuated container 16. The indicia 52 may be in the form of graduations defined along the axial dimension of the housing 42.

Tape, elastic bandages or other suitable means are used to attach the housing 42 to the patient, so that a full evacuated collection container can be removed and replaced with a new evacuated collection container without disturbing the attachment of the drainage system 10 to the body of the patient.

In use, the end of the catheter tube 12 without the perforations 14 is secured to a puncturing needle (not shown) which is inserted into the wound at one point and forced to exit at a separate point. The catheter tube 12 is then drawn through the wound until the indicator mark 20 is visible. At this point, all of the perforations 14 are positioned within the wound and an airtight seal is achieved at the exit point of the catheter tube 12 from the wound. Further drawing of the catheter tube 12 may result in exposing some of the perforations 14 outside of the wound and thereby prevent the creation of suction inside the wound. The puncturing needle is removed from the catheter tube 14, which is then attached to the post 26 on the adapter 18. The wound is closed, and, upon insertion of the hollow needle 27 through the septum of the stopper 30, vacuum is activated throughout the system 10. Depending upon the amount of drainage available, the vacuum will begin to draw fluid through the perforations 14 and the catheter tube 12 into the container 16. The protective housing 42 is attached to the patient in any convenient location, and the container 16 and the guide flanges 28 of the adapter 18 are inserted firmly in the housing 42.

Although it is apparent from the foregoing that the present invention is well adapted for application to the drainage of wounds, it is understood that the scope of the present invention is not so limited, but rather extends to other fluid handling applications. Also, various other changes and modifications may be made without departing from the spirit and scope of the present invention as recited in the appended claims and their legal equivalent.

What is claimed is:

1. A surgical drainage system comprising:
a catheter tube; an evacuated container having a pierceable stopper; and
an adapter for connecting the catheter tube to the container, the adapter including a body, a post projecting from the body for receiving the catheter tube, a hollow needle extending from the body, and a pair of guide flanges extending from the body on opposite sides of the needle and engaging the stopper to guide the adapter into a position on the container in which the needle pierces the stopper, said hollow needle, said body, and said post defining a passageway from said catheter tube to the interior of said container when said catheter tube is received on said post and said needle pierces said stopper.

2. The system of claim 1 further comprising a housing receiving said container, said housing having an opening defined by a peripheral wall having an internal surface, said guide flanges having outer surfaces complementary to the internal surface of the peripheral wall, whereby the guide flanges are frictionally retained within said opening.

3. The system of claim 2, wherein the guide flanges are arcuate and the internal surface of said peripheral wall includes a pair of opposed arcuate surfaces, the guide flanges being in frictional engagement with the arcuate surfaces.

4. The system of claim 3 wherein the guide flanges include free ends distal to the body of the adapter, the guide flanges being tapered toward the needle at their free ends and the outer surfaces of the guide flanges being spaced apart at their free ends a distance substantially equal to the distance between the opposed arcuate surfaces, so that, as the guide flanges of the adapter are moved into the opening of the housing, they are frictionally retained with increasing force.

5. The system of claim 3 wherein the container is cylindrical and the radius of curvature of said arcuate surfaces of said peripheral wall is greater than the outer radius of the container, whereby spaces are defined between the container and the arcuate surfaces of said peripheral wall for accommodating the arcuate guide flanges.

6. The system of claim 2 wherein the guide flanges include free ends distal to the body of the adapter, the guide flanges being inclined toward the needle at their free ends and the outer surfaces of the guide flanges being spaced apart at their free ends a distance substantially equal to the distance between opposite points on the internal surface of said peripheral wall, so that as the guide flanges of the adapter are moved into the opening of the housing, they are frictionally retained with increasing force.

7. The system of claim 2 wherein the body of the adapter includes a base which extends beyond said peripheral wall of the housing to define means for gripping the adapter for removal of the adapter from the housing.

8. The system of claim 2 wherein the housing is translucent.

9. The system of claim 8 wherein the housing includes indicia for measuring the volume of material in the container.

10. The system of claim 1 wherein the catheter tube includes a plurality of perforations adjacent one end and an indicator mark located a predetermined distance from the perforations to indicate where to stop drawing the tube through the wound.

11. The system of claim 1 wherein the needle is integral with the adapter body.

12. The system of claim 1 wherein a radio-opaque stripe extends along the length of the catheter tube, so that the tube may be easily located on a radiograph.

13. The system of claim 1 wherein each guide flange includes a free end distal to the body of the adapter and a pair of lateral edges extending between the free end and the body, adjacent lateral edges of the opposed guide flanges defining gaps exposing the stopper of the container to engagement by the fingers of a user, whereby the stopper can be held in place on the container when the adapter is removed.

14. The system of claim 13 wherein the body of the adapter includes side surfaces which lie in planes defined by the adjacent lateral edges of the opposed guide flanges.

* * * * *